United States Patent
Kim et al.

(10) Patent No.: US 9,285,371 B2
(45) Date of Patent: Mar. 15, 2016

(54) METHOD OF SCREENING ANTIBODIES WITH HIGH ANTIGEN SELECTIVITY

(71) Applicant: Samsung Electronics Co., Ltd., Suwon-si, Gyeonggi-do (KR)

(72) Inventors: Min-Kyung Kim, Seoul (KR); Jae-Il Lee, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/194,152

(22) Filed: Feb. 28, 2014

(65) Prior Publication Data
US 2014/0243507 A1    Aug. 28, 2014

(30) Foreign Application Priority Data

Feb. 28, 2013  (KR) ..................... 10-2013-0022454

(51) Int. Cl.
| | | |
|---|---|---|
| *C12N 15/13* | (2006.01) | |
| *G01N 33/68* | (2006.01) | |
| *C07K 16/00* | (2006.01) | |
| *C07K 16/18* | (2006.01) | |
| *G01N 33/53* | (2006.01) | |
| *G01N 33/574* | (2006.01) | |
| *C12N 15/10* | (2006.01) | |

(52) U.S. Cl.
CPC ........ *G01N 33/57492* (2013.01); *C07K 16/005* (2013.01); *C07K 16/18* (2013.01); *C12N 15/1037* (2013.01); *G01N 33/53* (2013.01); *G01N 33/6854* (2013.01); *G01N 33/6893* (2013.01); *C07K 2317/14* (2013.01); *G01N 2800/24* (2013.01)

(58) Field of Classification Search
CPC ..... C12N 15/1034; C40B 30/04; C40B 30/00
See application file for complete search history.

(56) References Cited

U.S. PATENT DOCUMENTS

| | | | |
|---|---|---|---|
| 5,011,912 A | * | 4/1991 | Hopp et al. ................. 530/387.9 |
| 2007/0172900 A1 | * | 7/2007 | Cahill et al. ................. 435/7.23 |
| 2010/0279881 A1 | | 11/2010 | Sompuram et al. |
| 2012/0034209 A1 | | 2/2012 | Perretti et al. |
| 2014/0234340 A1 | * | 8/2014 | Igawa et al. ................. 424/172.1 |

FOREIGN PATENT DOCUMENTS

| | | | | |
|---|---|---|---|---|
| JP | 2010-209085 A | | 9/2010 | |
| WO | WO 2007/092028 A2 | | 8/2007 | |
| WO | WO 2011/154705 A1 | * | 12/2011 | ............. C07K 16/18 |
| WO | WO 2012/073992 | * | 6/2012 | ............. C12N 15/09 |

OTHER PUBLICATIONS

Macmillan Dictionary (Kit, http://www.macmillandictionary.com/dictionary/american/kit, retrieved Aug. 23, 2013).*
He et al. (Bioengineered, Jan./Feb. 2013, 4:1 55-58).*
Gerke et al., Annexins: From Structure to Function, *Physiol. Rev.*, 82: 331-371 (2002).
Jespers et al., Epitope Mapping by Negative Selection of Randomized Antigen Libraries Displayed on Filamentous Phage, *J. Mol. Biol.*, 269: 704-718 (1997).
Gerke et al., "Annexins: From Structure to Function", *Physiol. Rev.* 82: 331-371 (2002).
Oh et al., "Subtractive proteomic mapping of the endothelial surface in lung and solid tumours for tissue-specific therapy", *Nature*, 429: 629-635 (2004).
Rescher et al., "Annexins—unique membrane binding proteins with diverse functions", *Journal of Cell Science*, 117: 2631-2639 (2004).

* cited by examiner

*Primary Examiner* — Peter J Reddig
(74) *Attorney, Agent, or Firm* — Leydig, Voit & Mayer, Ltd.

(57) ABSTRACT

Provided is a method of screening a target-specific antibody for an antigen that undergoes structural change in a particular physiological condition.

9 Claims, 3 Drawing Sheets

METHOD OF SCREENING ANTIBODIES WITH HIGH ANTIGEN SELECTIVITY

CROSS-REFERENCE TO RELATED APPLICATIONS

This application claims the benefit of Korean Patent Application No. 10-2013-0022454, filed on Feb. 28, 2013, in the Korean Intellectual Property Office, the disclosure of which is incorporated herein in its entirety by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 6,416 ASCII (Text) file named "716223_ST25-Revised," created Jul. 15, 2015.

BACKGROUND OF THE INVENTION

1. Field

The present disclosure relates to a method of screening antibodies with high antigen selectivity, and in particular, to a method of screening antibodies with high selectivity for an antigen that undergoes structural change in a particular physiological condition.

2. Description of the Related Art

An antibody that binds to an antigen is, in general, specific to a single antigen, and the binding has high affinity. An antibody is generated by a B-lymphocyte. Blood has many different antibodies, each of which is derived from a clone of a B-cell and has a particular structure and specificity to an antigen.

Lipocortin, calpoxin, and endonexin have commonly been referred to as annexin over a decade Annexin binds to calcium and phospholipid, and has a particular and preserved domain in which a 70-amino acid sequence having 'GXGTDE' motif (SEQ ID NO: 3) called endonexin-fold is repeated four times (or 8 times). Conventionally disclosed Annexin proteins include the preserved domain, and Annexin protein is identified based on the inclusion of the preserved domain.

Annexin protein is known to exist in various living organisms ranging from mammals to filamentous fungus, and it is reported that Annexin I, II, III, IV, V, VI, VII, VIII, and XIII are derived from human beings. Annexin protein is known to be involved in various biological phenomena, including formation of bone structure, membrane trafficking, membrane permeable channel activities, inhibition of phospholipase A2, inhibition of coagulation, delivery of mitogen signals, and cell-matrix interaction control. Also, Annexin A1, from among Annexin proteins, is known to be found in cancer tissues. Also, research into development of anticancer drugs by using a protein that is over-expressed in cancer cells is being performed.

Typically, as a method of screening an antibody for a particular antigen, screening using a phage displayed antibody library is often used. In general, however, a disease target protein, such as an anticancer protein, is involved in various signal transduction systems, and in the case of an antigen that undergoes structural change dependent on surrounding environments, the typical library screening is not enough to screen out an antibody that has high affinity.

Accordingly, inventors of the present application studied and designed a method of screening an antibody with high selectivity.

SUMMARY OF THE INVENTION

Provided are methods of screening antibodies with high antigen selectivity, the method including: contacting an antigen protein with calcium ($Ca^{2+}$) or calcium salts; and contacting an antibody library with the antigen protein in the presence of the calcium or calcium salt.

Also provided are antibodies obtained by using the methods of screening.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE INVENTION

Figure 1:
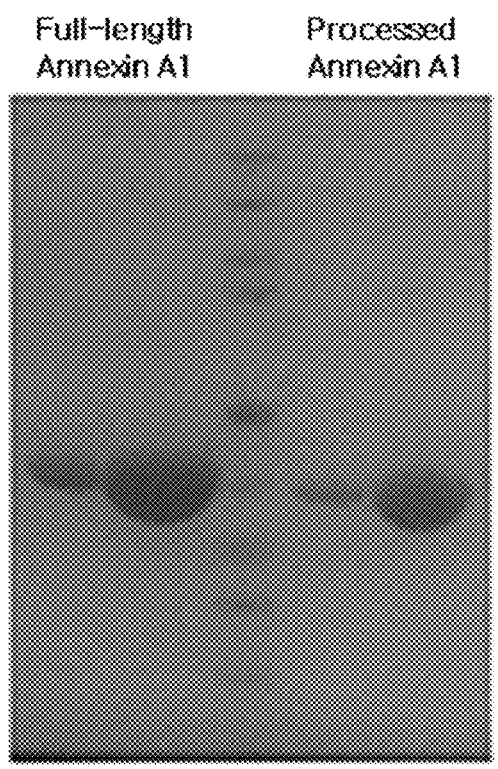
FIG. 1 is a gel separation showing two forms of purified Annexin A1: the left-hand column shows full-length protein of Annexin A1, and the right-hand column shows a truncated form of Annexin A1.

According to an aspect of the present invention, provided is a method of screening an antibody with high selectivity.

According to an embodiment of the present invention, the method includes contacting an antigen protein with calcium ($Ca^{2+}$) or calcium salts; and contacting an antibody library (Ab library) with the antigen protein that contacts the calcium ($Ca^{2+}$) or calcium salts. The method of screening an antibody will now be described in detail.

An antigen protein is brought into contact with calcium (Ca2+) or a calcium salt. For use as the antigen protein, any kind of intracellular, extracellular, or cell membrane-bound protein may be used. The antigen protein may be used as a disease target protein, such as a protein related to cancer or a protein related to immune disease. The antigen protein participates in various signal transduction systems, and may be an antigen protein that undergoes structural change in dependence on an upstream signal from among the signal transduction systems. Also, the antigen protein may be a protein that undergoes structural change according to a change in the concentration of calcium ion secreted in response to an upstream signal. The antigen protein may be a full-length protein, or a protein that has an N-terminal or C-terminal that is truncated.

For example, the antigen protein may be Annexin. According to an embodiment of the present invention, the antigen protein may be Annexin A1, but is not limited thereto. According to another embodiment of the present invention, the antigen protein may be selected from the Annexin family including Annexin A1, EF hand protein, such as calmodulin, troponin C, or S100 protein, and C2 domain protein, such as protein kinase C. The antigen protein Annexin A1 may be a full-length protein, and may include a polypeptide having a sequence set forth in SEQ ID NO: 1. Also, the antigen protein Annexin A1 may be a protein of which N-terminal is truncated (e.g., a polypeptide set forth in SEQ ID NO: 2).

To contact an antigen protein with calcium or calcium salts, calcium may be added to a sample including the antigen protein. The concentration of calcium or calcium salts to be added may be in a range of about 0.1 to about 30 nM, (e.g., about 0.5 to about 30 nm, or about 0.5 to about 15 nm, about 1 to about 10 nm, about 1 to about 5 nm, or about 1 to about 3 nM). However, the calcium concentration is not limited to these ranges described above. The calcium concentration may be appropriately controlled according to an antigen protein in view of conventional knowledge of one of ordinary skill in the art. Examples of calcium salts are calcium chloride ($CaCl_2$), potassium chloride (KCl), or sodium chloride (NaCl).

The calcium or calcium salt, or the sample containing the antigen protein to which the calcium or calcium salt is added, can have any suitable carrier (e.g., liquid carrier). Suitable carriers include an aqueous solution, for example, water, aqueous buffer, or a combination thereof.

Subsequently, an antibody library (Ab library) is contacted with to the antigen protein in the presence of the calcium solution.

The antibody library may be a phage display library. The phage display library (also referred to as phage peptide/antibody library, phage library or peptide/antibody library) includes a large phage group (in general, in a range of about $10^8$ to about $10^9$), and phage particles display different peptide or polypeptide sequences. These peptide or polypeptide fragments may be prepared in various lengths. The displayed peptide or polypeptide may be derived from a heavy chain or a light chain of human antibody, but is not limited thereto.

Phage clones are selected and identified by using a multi-step process known as biopanning. Biopanning is performed as follows: a phage display protein ligand mutant is mixed with a target maintaining a constant temperature; non-bound phage display protein ligand mutants are removed by washing, and bound phage display protein ligand mutants are specifically eluted. The phage display protein ligand mutant obtained by the elution is amplified before an additional binding cycle is performed to provide a concentrated pool of the sequences of the phage clones that produce an antibody fragment that displays optimal binding with respect to a target. After several cycles of the above biopanning procedure, individual phage clones are specified, and the sequence of a peptide or antibody displayed by the clone is determined by sequencing DNA corresponding to protein displayed in phage.

Additionally, the antibody library may be subjected to negative selection. The negative selection is performed, for example, to screen an antibody that specifically and selectively binds to a truncated antigen protein over the full-length antigen. The negative selection may be performed by contacting the antibody library with the full-length antigen protein, and removing those antibodies (clones) from the library that bind to the full-length antigen protein from the antibody library. Due to the negative selection, a peptide or antibody that is bindable to an antigen full-length protein is removed from the antibody library. Accordingly, the resultant antibody library has a higher concentration of antibodies (phage clones expressing antibodies) with selectivity for the truncated antigen protein.

An embodiment of the present invention provides an antibody or antibody fragment with high selectivity.

An antibody or antibody fragment according to an embodiment of the present invention may be an antibody or antibody fragment that is obtained from an antibody library obtained by using the screening.

The "antibody" used herein has a broad meaning, and in detail, includes a monoclonal antibody, polyclonal antibody, dimer, polymer, multi-specific antibody (for example: double-specific antibody), and an antibody fragment displaying target biological activities. An antibody may be derived from murine, human beings, the humanized, chimera, or other species. An antibody is a protein that recognizes and binds a specific antigen and that is generated by an immune system.

An antibody may be a full-length immunoglobulin molecule or an immunologically active portion thereof, that is, a target antigen (including, for example, cancer cell, or cell for generating autoimmunity antibodies associated with autoimmunity disease), or a molecule containing an antigen binding site that immuno-specifically binds to a portion of the target antigen.

The term "antibody fragment" used herein includes a part of a full-length antibody, in general, an antigen bindable or variable region thereof. Examples of an antibody fragment are Fab, Fab', $F(ab')_2$, and Fv fragment; diabody; a linear antibody; a fragment generated by Fab-expression library, an anti-individual specific (anti-Id) antibody, a complementarity determining region (CDR), and an epitope-bindable fragment of the antibody that immune-specifically binds an cancer cell antigen, viral antigen, or a microbial antigen; a single chain antibody molecule; and a multi-specific antibody formed from an antibody fragment.

In addition, the antibody may be an antibody that specifically binds to Annexin A1. In particular, an antibody selected by the negative selection may specifically bind only to a truncated protein obtained by cleaving, not a full-length protein.

An embodiment of the present invention provides a kit for diagnosing disease, such as cancer or inflammatory disease, including the antibody.

The term "cancer" and "cancerous" used herein means or explains a physiological state featured as uncontrollable cell growth in mammals. The term "tumor" includes one or more cancerous cells. Examples of cancer are carcinoma, lymphoma, blastoma, sarcoma, and leukemia or lymphocytic malignant tumor, but are not limited thereto. Detailed examples of cancer are squamous cell cancer (for example, epithelial squamous cell cancer); lung cancer, such as small-cell lung cancer, non-small cell lung cancer ("NSCLC"), adeno carcinoma of lung, and squamous carcinoma of lung; peritoneal cancer, hepatocellular cancer; gastric cancer, such as gastrointestinal cancer; pancreas cancer, gliobblastoma, cervical cancer, ovarian cancer, liver cancer, bladder cancer, hepatoma, breast cancer, colorectal cancer, rectal cancer, rectal colon cancer, endometrial or uterus carcinoma, salivary glands carcinoma, kidney cancer, prostate cancer, pudendum cancer, thyroid cancer, liver carcinoma, anal carcinoma, penis carcinoma, and head and neck cancer.

Also, the kit may be provided as a kit including a package unit having one or more reaction reagents. Also, the kit may include one or more of the following items: a buffer solution, instruction manual, and a positive or negative control group. The kit may include vials for reaction reagents that are mixed at an appropriate ratio to perform the method described above. The vials include unit amounts of reaction reagents to omit a measurement process when the method is performed.

Hereinafter, embodiments of the present invention are described in detail in Examples. However, Examples are for illustrative purpose only, and do not limit embodiments of the present invention, which is obvious to one of ordinary skill in the art.

Example 1

Acquisition of Annexin A1 Protein and Truncated Annexin A1 (ANX A1) Protein

A vector for expressing full-length Annexin A1 (SEQ ID NO: 1) and truncated Annexin (SEQ ID NO: 2) in *E. coli* was synthesized (Genotech). The synthesized vector was transformed into *E. coli* and cultured overnight, Affinity purification was performed using a His tag of the expressed Annexin and truncated Annexin protein-terminal. Purity and size of purified full-length and truncated Annexin protein were determined by electrophoresis in a polyacrylamide gel (FIG. 1). The truncated Annexin protein is herein after referred to as the "processed" form of Annexin.

Example 2

Screening of Anti ANX A1 Antibody

To screen an antibody that is specific to the processed form ANX A1, from among two forms (WT form and Processed form) of Annexin A1 (ANX A1) antigen in vivo, negative selection was performed by using a full-length Annexin protein to eliminate antibodies binding to full length Annexin, and the remaining antibody pool was screened for an antibody binding to a truncated Annexin protein by biopanning.

To perform the biopanning, biotin was attached to full-length Annexin protein by using a biotinylation kit (Pierce), and then, was bound to streptavidin-coated magnetic beads (Invitrogen). An antibody library, a synthetic scFv library from Ewha University, was bound to the protein binding to beads, so that an antibody library other than antibodies binding to full-length Annexin protein was obtained by negative selection. Likewise, truncated Annexin A1 (processed ANX A1) with biotin attached thereto was bound to magnetic beads, and the remaining antibody library that had undergone the negative selection was bound to the beads by submerging in a solution including 2 mM $CaCl_2$ and TBS (Tris-buffered saline) for the duration of the experiment to obtain an antibody that specifically binds to truncated ANX A1. This process, that is, a positive selection process was repeatedly performed using the antibodies selected in the prior screen, up to round 3 to enhance an antibody pool from which a non-specific binding to truncated Annexin was removed.

Example 3

Identification of Binding Force of Selected Antibody

Figure 2:
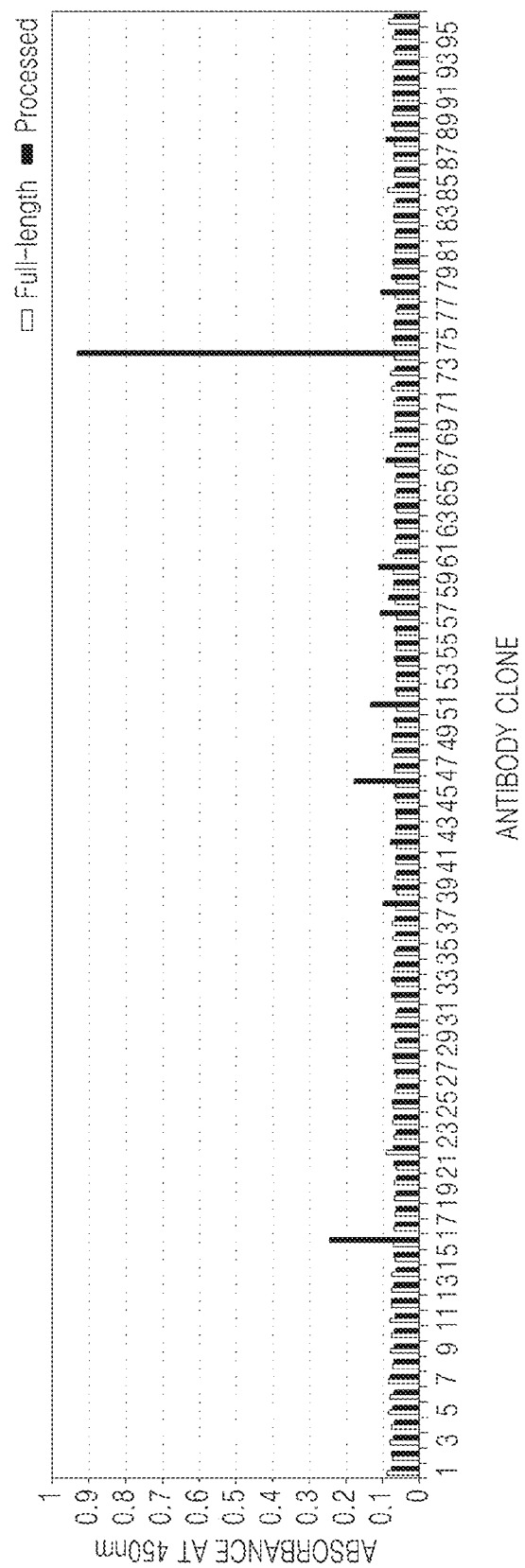
FIG. 2 is a graph showing binding results between an antigen and an antibody sub-library selected by a second library screening (Round 2), wherein the Y axis shows antibody affinity to the antigen used for screening and the X axis shows the selected antibody clones binding to one of two screening antigens. The Y axis refers to OD450, i.e., light absorbance at a wavelength of 450 nm, which is used as a unit for representing intensity of a reaction in an ELISA assay. The screening used a full-length Annexin protein and a truncated Annexin protein as antigens.
Figure 3:
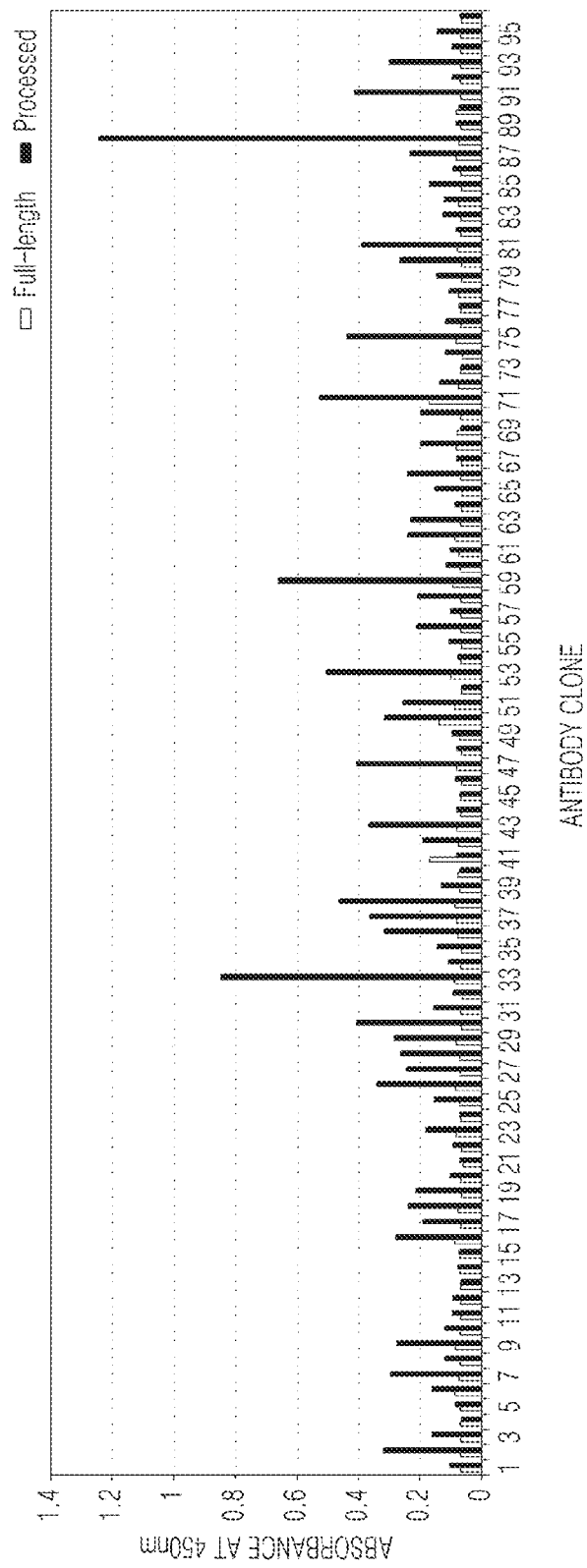
FIG. 3 is a graph showing binding results between an antigen and an antibody sub-library selected by a third library screening (Round 3), wherein the Y axis shows antibody affinity to the antigen used for screening and the X axis shows the selected antibody clones binding to one of two screening antigens. The Y axis refers to OD450, i.e., light absorbance at a wavelength of 450 nm, which is used as a unit for representing intensity of a reaction in an ELISA assay. The screening used a full-length Annexin protein and a truncated Annexin protein as antigens.

To identify the binding force of the antibody library selected by biopanning with respect to an antigen, an antigen binding test was performed by ELISA. *E. coli* infected with an individual phage clone was cultured overnight, and then, a periplasmic fraction including a phage displayed antibody was separated by using 20% sucrose solution. The periplasmic fraction was bound to a full-length Annexin and truncated Annexin-coated 96-well immunoplate (Nunc), and then, bound to a secondary antibody (Santa Cruz) that detects an HA tag that is tagged at an antibody-terminal. The secondary antibody used herein was an antibody conjugated with HRP. The round 2 and round 3 results of the biopanning are shown in FIGS. 2 and 3, respectively. The results show that antibodies selective to truncated Annexin can be identified by the method described herein.

As described above, one or more of the above embodiments of the present invention provide a method of screening an antibody for an antigen that undergoes structural change in a particular physiological condition. The structural change includes a structural change caused by an ion state, in particular, calcium, and a structural change induced by truncating a portion of a terminal of an antigen protein when the antigen protein binds to a cell membrane. An antibody selected by using the method has high selectivity with respect to an antigen that is dependent on a particular condition and structural change. Accordingly, the antibody may be effectively used for the diagnosis and treatment using an antibody.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of screening antibodies, the method comprising:
   contacting an antigen protein with a solution of calcium or calcium salt, wherein the antigen protein is a truncated version of a wild-type protein of interest;
   performing a negative selection on an antibody library, wherein the negative selection comprises contacting the library with a full-length version of the wild type protein of interest and removing any antibody bound to the full-length version of the wild type protein of interest from the antibody library;
   contacting the antibody library with the antigen protein in the presence of the calcium or calcium salt; and
   selecting one or more antibody or antibody fragments from the antibody library with the highest binding affinity to the antigen protein.

2. The method of claim 1, wherein the antigen protein is a truncated version of a wild-type protein selected from the group consisting of Annexin, calmodulin, EF hand protein, and C2 domain protein.

3. The method of claim 2, wherein the antigen protein is a truncated version of Annexin A1 protein.

4. The method of claim 3, wherein the Annexin A1 protein has an amino acid sequence set forth in SEQ ID NO: 1.

5. The method of claim 1, wherein the antigen protein is an Annexin A1 protein with a truncated N-terminal or C-terminal.

6. The method of claim 2, wherein the Annexin has an N-terminal that is truncated.

7. The method of claim 6, wherein the Annexin having the N-terminal that is truncated has an amino acid sequence set forth in SEQ ID NO: 2.

8. The method of claim 1, wherein the antibody library is a phage display library.

9. The method of claim 5, wherein the negative selection comprises contacting the antibody library with an Annexin full-length protein, and removing an antibody bound to the Annexin full-length protein from the antibody library.

\* \* \* \* \*

```
                          SEQUENCE LISTING

<160> NUMBER OF SEQ ID NOS: 3

<210> SEQ ID NO 1
<211> LENGTH: 346
<212> TYPE: PRT
<213> ORGANISM: Artificial Sequence
<220> FEATURE:
<223> OTHER INFORMATION: Synthetic (Annexin A1 protein)

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
```

<210> SEQ ID NO 2
<211> LENGTH: 316
<212> TYPE: PRT
<213> ORGANISM: Artificial Sequence
<220> FEATURE:
<223> OTHER INFORMATION: Synthetic (truncated Annexin A1 protein)

<400> SEQUENCE: 2

```
Gly Pro Gly Ser Ala Val Ser Pro Tyr Pro Thr Phe Asn Pro Ser Ser
 1               5                  10                  15

Asp Val Ala Ala Leu His Lys Ala Ile Met Val Lys Gly Val Asp Glu
             20                  25                  30

Ala Thr Ile Ile Asp Ile Leu Thr Lys Arg Asn Asn Ala Gln Arg Gln
         35                  40                  45

Gln Ile Lys Ala Ala Tyr Leu Gln Glu Thr Gly Lys Pro Leu Asp Glu
     50                  55                  60

Thr Leu Lys Lys Ala Leu Thr Gly His Leu Glu Glu Val Val Leu Ala
 65                  70                  75                  80

Leu Leu Lys Thr Pro Ala Gln Phe Asp Ala Asp Glu Leu Arg Ala Ala
                 85                  90                  95

Met Lys Gly Leu Gly Thr Asp Glu Asp Thr Leu Ile Glu Ile Leu Ala
            100                 105                 110

Ser Arg Thr Asn Lys Glu Ile Arg Asp Ile Asn Arg Val Tyr Arg Glu
        115                 120                 125

Glu Leu Lys Arg Asp Leu Ala Lys Asp Ile Thr Ser Asp Thr Ser Gly
130                 135                 140

Asp Phe Arg Asn Ala Leu Leu Ser Leu Ala Lys Gly Asp Arg Ser Glu
145                 150                 155                 160

Asp Phe Gly Val Asn Glu Asp Leu Ala Asp Ser Asp Ala Arg Ala Leu
                165                 170                 175

Tyr Glu Ala Gly Glu Arg Arg Lys Gly Thr Asp Val Asn Val Phe Asn
            180                 185                 190

Thr Ile Leu Thr Thr Arg Ser Tyr Pro Gln Leu Arg Arg Val Phe Gln
        195                 200                 205

Lys Tyr Thr Lys Tyr Ser Lys His Asp Met Asn Lys Val Leu Asp Leu
    210                 215                 220

Glu Leu Lys Gly Asp Ile Glu Lys Cys Leu Thr Ala Ile Val Lys Cys
225                 230                 235                 240

Ala Thr Ser Lys Pro Ala Phe Phe Ala Glu Lys Leu His Gln Ala Met
                245                 250                 255

Lys Gly Val Gly Thr Arg His Lys Ala Leu Ile Arg Ile Met Val Ser
            260                 265                 270

Arg Ser Glu Ile Asp Met Asn Asp Ile Lys Ala Phe Tyr Gln Lys Met
        275                 280                 285

Tyr Gly Ile Ser Leu Cys Gln Ala Ile Leu Asp Glu Thr Lys Gly Asp
    290                 295                 300

Tyr Glu Lys Ile Leu Val Ala Leu Cys Gly Gly Asn
305                 310                 315
```

<210> SEQ ID NO 3
<211> LENGTH: 6
<212> TYPE: PRT
<213> ORGANISM: Artificial Sequence
<220> FEATURE:
<223> OTHER INFORMATION: Synthetic -continued

```
<220> FEATURE:
<221> NAME/KEY: misc_feature
<222> LOCATION: (2)..(2)
<223> OTHER INFORMATION: Xaa can be any naturally occurring amino acid

<400> SEQUENCE: 3

Gly Xaa Gly Thr Asp Glu
1               5
```